United States Patent [19]

Zehner

[11] 4,069,388
[45] * Jan. 17, 1978

[54] PREPARATION OF OXALATE ESTERS FROM CARBON MONOXIDE AND AN ALKOXYCYCLOALKENE

[75] Inventor: Lee R. Zehner, Media, Pa.

[73] Assignee: Atlantic Richfield Company, Los Angeles, Calif.

[*] Notice: The portion of the term of this patent subsequent to Dec. 27, 1994, has been disclaimed.

[21] Appl. No.: 734,799

[22] Filed: Oct. 22, 1976

[51] Int. Cl.$^2$ .................. C07C 67/36; C07C 69/36
[52] U.S. Cl. .................................. 560/204; 560/193; 560/196; 560/198
[58] Field of Search ............ 260/485 R, 485 L, 485 J, 260/485 P, 465 D

[56] References Cited

U.S. PATENT DOCUMENTS 3,393,136  7/1968  Fenton et al. .................. 260/485 R

FOREIGN PATENT DOCUMENTS 2,213,435  10/1973  Germany .............................. 260/485
2,514,685  10/1975  Germany .............................. 260/485

OTHER PUBLICATIONS

Fenton et al., J. Org. Chem., 39 No. 5, 701–704 (1974).

Primary Examiner—Jane S. Myers
Attorney, Agent, or Firm—Delbert E. McCaslin

[57] ABSTRACT

A process for the preparation of oxalate esters by the catalytic oxidative carbonylation of an alkoxycycloalkene with carbon monoxide, an alcohol and oxygen or an oxygen-containing gas in the presence of a metal salt catalyst and an amine base. In addition, a catalytic amount of particular metal oxidizing salts is employed along with a catalytic amount of an acid or an amine salt compound. Alternatively various counterions and ligands of the metal salt catalysts may be employed.

26 Claims, No Drawings

PREPARATION OF OXALATE ESTERS FROM CARBON MONOXIDE AND AN ALKOXYCYCLOALKENE

BACKGROUND OF THE INVENTION

A number of prior art processes have been proposed for the preparation of oxalate esters by the oxidative carbonylation of alcohols in the presence of metal salt catalysts, dehydrating agents and ferric or cupric redox agents in solution.

The present invention is directed to a process for the preparation of oxalate esters in high yield and avoiding the problems associated with the prior art processes of carbonylating alcohols directly to obtain the desired oxalate ester. More particularly, the present process relates to the synthesis of oxalates by reacting carbon monoxide, a particular amount of an alcohol, and oxygen with an alkoxycycloalkene under elevated temperature and pressure conditions in the presence of a catalytic amount of a palladium, platinum, cadmium, cobalt, rhodium, zinc or copper salt catalyst and at least a catalytic amount of an amine base and includes the employment of catalytic amounts of copper (II) or iron (III) oxidant salts in addition to catalytic amounts of an ammonium or substituted ammonium salt compound and ligands of the metal salt catalysts.

U.S. Pat. No. 3,393,136 describes a process for the preparation of oxalates by contacting carbon monoxide at superatmospheric pressure, with a saturated monohydric alcohol solution of a platinum group metal salt and a soluble ferric or cupric salt (redox agent) while maintaining the salts in a highly oxidized state by the simultaneous introduction of oxygen or the application of a direct current electrical potential to the reaction zone. When oxygen is employed, explosive mixtures of oxygen and combustible organic vapors in the gas phase must be avoided and water scavengers or dehydrating agents such as alkyl orthoformic acid esters must be added to the liquid phase to provent the accumulation of water.

In a recent article by Donald M. Fenton and Paul J. Steinwand, Journal of Organic Chemistry, Vol. 39, No. 5, 1974, pp. 701-704, a general mechanism for the oxidative carbonylation of alcohols to yield dialkyl oxalates using a palladium redox system, oxygen and dehydrating agents has been proposed. In the absence of the necessary dehydrating agent, a large amount of carbon dioxide is formed and oxalates are not produced. The necessity of the iron or copper redox system during the oxalate synthesis is emphasized.

A recent West German Pat. No. 2,213,435 discloses a method for the synthesis of oxalic acid and oxalate esters using water and alcohol respectively. A platinum group metal salt, a salt of a metal more electropositive than the platinum group metal, e.g., copper (II) chloride and an alkali metal salt comprise the catalyst. Oxygen is stoichiometric amounts was employed as the oxidant. A disadvantage of such reaction is that explosive mixtures of oxygen and carbon monoxide are necessary to effect reaction. Under non-explosive conditions only trace amounts of oxalate can be obtained.

A more recent West German Pat. No. 2,514,685 describes a process for the production of dialkyl oxalates by reacting an aliphatic alcohol with CO and oxygen under pressure in the presence of a catalyst comprising a mixture of a salt of a metal from the platinum group and a salt of copper or iron and an accelerator including nitrates, sulfates, carbonates, tertiary amines and hydroxides and carboxlates of alkali metals and alkaline earth metals. Conversion of the alcohol employed to the dialkyl oxalates in such process is low.

Many important commercial applications have been developed for the oxalate products of this invention, for example, as cellulose ether or ester and resin solvents, as dye intermediates and the preparation of ethylene glycol.

The process of the present invention provides a method of carrying out the oxidative carbonylation of an alkoxycycloalkene to produce an oxalate ester without the coproduction of water which acts to poison the catalyst system and which even in small amounts also causes the production of large quantities of carbon dioxide and an attendant loss of the desired oxalate ester. Thus, by the process of the present invention, only very small concentrations of water can accumulate in the reaction system since by the mechanism of the reaction any water which might be formed is rapidly consumed upon formation of coproduct ketone. In addition, the coproduction of carbonate esters associated with such carbonylation reactions is minimized giving excellent selectivities to oxalate esters with high conversions of the alkoxycycloalkene. The cyclic ketone coproduced with the desired oxalate ester by the oxidative carbonylation reaction of the alkoxycycloalkene may be readily separated from the desired oxalate and converted back to the respective reactant alkoxycycloalkene.

Other advantages of the present invention, as compared to known prior art processes for the production of oxalates are (1) elimination of hazardous operational conditions by avoiding explosive mixtures of oxygen and carbon monoxide, (2) avoiding the use of large amounts of corrosive chloride ions (3) ease of recovery and regeneration of the metal salts catalysts for reuse in the process and (4) the ability to employ in the process as catalysts the more readily available copper salts and other metal salts in place of the more expensive platinum group metal salts.

SUMMARY OF THE INVENTION

According to the present invention there is provided a much improved catalytic oxidative carbonylation process for the preparation in high yield of oxalate esters by reacting stoichiometric quantities of an alcohol, carbon monoxide and oxygen with an alkoxycycloalkene, which process is carried out at elevated temperatures and pressures in the presence of a metal salt catalyst and at least a catalytic amount of an amine base and under relatively anhydrous conditions. In the process at least one mole of alcohol per mole of alkoxycycloalkene is employed. The process of the invention also utilizes, in appropriate catalytic amounts, particular metal oxidant salts and an acid or an ammonium or substituted ammonium salt compound to provide a pronounced effect on oxalate ester selectivity, and high conversions to the oxalates over the carbonates which may be present in only trace amounts. In addition, it has been found that alternatively catalytic amounts of various ligands, which will not work in themselves, may be used as co-catalysts in conjunction with the metal salt catalysts, the amines, the amine salts and the oxidant salts.

It is a primary object of this invention to provide a process for the preparation of oxalate esters in high yield and high conversion of reactants while avoiding operational problems associated with prior processes.

It is another object of this invention to provide a novel reaction system useful in the conversion of carbon monoxide, oxygen, alcohol and alkoxycycloalkenes to oxalate esters.

It is a further object of this invention to provide a specific mechanism for the employment of catalysts, oxidant salts, amine salts and amines in an oxidative carbonylation process employing alkoxycycloalkenes as reactants.

These and other objects and advantages of this invention will become apparent from the description of the invention which follows and from the claims.

DESCRIPTION OF THE INVENTION

In accordance with the invention, an oxalate ester is produced by reacting, under relatively anhydrous liquid phase conditions, an alkoxycycloalkene with carbon monoxide, at least equal molar quantities of an alcohol based on the alkoxycycloalkene employed and oxygen at elevated temperatures and pressures in the presence of a catalyst comprising palladium, rhodium, platinum, copper, cobalt, cadmium or zinc metal salts, with or without a ligand such as lithium iodide as a co-catalyst, and in catalytic amounts, ammonia or a primary, secondary or tertiary amine and in addition catalytic amounts of a copper (II) or iron (III) metal oxidant salt, an ammonium salt or amine salt, or while employing an excess of the amine base, an acid stronger than water which will not complex too strongly with the metal salt catalyst. The synthesis of the oxalate esters is carried out according to the following postulated equation:

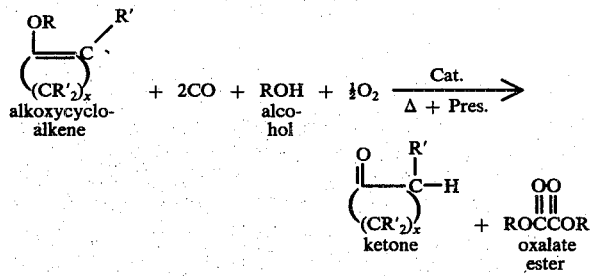

wherein R is an alkyl or aralkyl group, which may be the same or different, R' is hydrogen or a straight or branched chain alkyl group which may be the same or different on the cyclic ring. When R and R' are alkyl groups they may be the same or different. x is an integer of from 3 to 6. When the R of the alkoxycycloalkene and the alcohol are different, mixed oxalate esters, e.g., methyl ethyl oxalate, are formed.

As indicated above, catalytic amounts of an amine are added to the reaction mixture and as noted, in addition, in catalytic amounts, a metal oxidant salt and an amine salt. The amine salt so added may also be formed in situ in the reaction mixture by the addition of an acid such as sulfuric acid in order to form the necessary quantity of amine salt. Thus, for example, triethylamine can be employed initially in sufficient amounts in excess over the catalytic amount and sulfuric acid added to form triethylammonium sulfate in the desired catalytic quantities. The addition of the amine salt maintains the proton acidity of the reaction system thereby providing an increased selectivity and yield of oxalate ester.

The reaction between the alkoxycycloalkene, carbon monoxide, alcohol and oxygen may be carried out in an autoclave or any other high pressure reactor. A general procedure is to charge the alkoxycycloalkene, amine, alcohol, amine salt (or the required amount of amine and acid), catalyst, and the oxidant salt into the reaction vessel, introduce the proper amount of carbon monoxide and oxygen to the desired reaction pressure and then heat the mixture to the desired temperature for the appropriate period. The reaction can be carried out batchwise or as a continuous process and the order of addition of the reactants may be varied to suit the particular conditions and apparatus employed. The reaction products are recovered and treated by any conventional method such as distillation and/or filtration, etc. to effect separation of the oxalate from unreacted materials, catalysts, oxidant salt, amine salt, by products, etc.

The alkoxycycloalkenes employed in stoichiometric quantities and suitable for use in the process of the present invention conform to the general formula

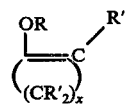

as indicated hereinabove. Representative of such compounds is, for example, 1-methoxy-4-ethylcyclohexene having the structural formula

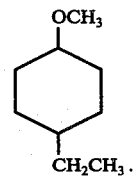

From 5 to 8 carbon atoms may be in the cyclic ring. R may be an alkyl group containing from 1 to 10 carbon atoms preferably 1 to 4 carbon atoms. R may also be an aralkyl group containing one or more benzenoid rings preferably not more than 2 rings which may be fused or joined by single valency bonds. R' may be hydrogen or a straight or branched chain alkyl group containing from 1 to 10 carbon atoms preferably from 1 to 4 carbon atoms in the alkyl chain. x is an integer of from 3 to 6 thus forming a cyclic ring which may have from 5 to 8 carbon atoms.

Representative alkoxycycloalkenes suitable for use in this invention include for example, 1-methoxy-, 1-ethoxy-, 1-propoxy-, 1-butoxy-, 1-isobutoxy-, etc. cyclohexenes, cycloheptenes, cyclopentenes, cyclooctenes, etc., 1-methoxy-4-methylcyclohexene, 1-methoxy-2-methyl-4-ethylcyclohexene, 1-ethoxy-4-butylcycloheptene, 1-methoxy-2-methyl-6-ethylcyclooctene, etc.

The alcohols employed in at least stoichiometric quantities with the alkoxycycloalkenes and suitable for use in the process of the present invention can be monohydric saturated aliphatic and alicyclic alcohols or aralkyl alcohols and may contain other substituents such as amido, alkoxy, amino, carboxy, cyano, etc. radicals in addition to the hydroxyl group. The substituents, in general, do not interfere with the reaction of the invention.

The alcohols which are employed in at least molar quantities equal to the molar quantities of alkoxycycloalkene employed may be primary, secondary or tertiary alcohols and conform to the general formula ROH, wherein R is an optionally substituted aliphatic or alicyclic group preferably containing from 1 to 10 carbon atoms. R may also be an aralkyl group containing one or more benzenoid rings preferably not more than 2 rings which may be fused or joined by single valency bonds, directly or through bridging groups which may be, for example, oxygen or sulfur atoms or sulfoxide, sulfone or carbonyl groups or alkylene groups in which, if desired, the carbon chain may be interrupted by, for example, oxygen or sulfur atoms, sulfoxide, sulfone or carbonyl groups, for example, methylene, oxymethylene, dimethylene sulfone or dimethylene ketone groups. Representative alcohols especially suitable for use in this invention are monohydric alcohols such as methyl, ethyl, n-, iso-, sec-, and tert-butyl, amyl, hexyl, octyl, n- and iso-propyl, benzyl, chlorobenzyl and methoxy-benzyl alcohols, as well as, for example, cyclohexanol, octanols, heptanols, decanols, 2-ethyl hexanol, nonanol, methyl cyclohexanol, and the like. The preferred alcohols are the primary and secondary monohydric alcohols, such as methanol, ethanol and n-butyl alcohol.

The amines employed in catalytic quantities in the process of the invention in addition to ammonia may by primary, secondary, or tertiary amines and include aliphatic, cycloaliphatic, aromatic and heterocyclic amines or mixtures thereof. The amines may be unsubstituted or contain other substituents such as halides, alkyl, aryl, hydroxy, amino, alkylamino, carboxy, etc. The amines may be employed in the reaction in concentrations of from 0.1 to 5 weight per cent and preferably at a concentration ~3 weight percent.

Representative amines as hereinabove described, include for example, mono-, di- and tri-methyl, ethyl, and propyl amines, iso- and diisopropylamines, allyl amines, mono-, di-, tri-, iso and diisobutyl amines, 1-methylpropyl amine, 1,1-dimethylethyl amine, amyl amines, cyclohexyl amine, dicyclohexylamine, 1,3-dimethylbutyl amine, 2-ethylhexylamine, 1-cyclopentyl-2-amino propane, 1,1,3-tetramethylbutylamine, aniline, ethylene diamine, methylene diamine, ethanolamine, octylamines, n-decyl amine, do-, tetra-, hexa-, octa-, dido-, ditetra-, diocta-, trido, and triocta-decylamines, chloroanilines, nitroanilines, toluidines, naphthylamine, N-methyl and N-ethyl, and N,N-dimethyl and N,N-diethyl aniline, di- and triphenylamines, N,N-diamylaniline, benzyl dimethyl amine, piperidine, pyrrolidine, etc. The preferred amines are the tertiary amines such as triethylamine and tributyl amine.

The metal salt catalysts which may be employed in the process of this invention are the palladium, platinum, rhodium, copper, cobalt, cadmium and zinc salts. Among the chemical forms of the metal compounds which can be used as such or as mixtures are the palladium, platinum and rhodium, halides, sulfates, oxalates and acetates and the copper halides preferably the palladium (II) and copper (I) or (II) halides such as palladium (II) chloride, palladium (II) iodide, copper (II) chloride and copper (I) iodide. Representative catalytic metal salt compounds include, for example palladium (II) chloride, copper (II) chloride, rhodium (III) chloride, copper (II) iodide, palladium (II) sulfate, palladium (II) oxalate, palladium (II) acetate, palladium (II) iodide, rhodium (III) bromide, platinum (II) chloride, platinum (II) sulfate, cobalt (II) chloride, cadmium chloride, zinc chloride, etc.

The catalysts employed may be in a homogeneous state in the reaction mixture at reaction conditions. Thus, the catalysts may be present in solution, or suspension and may also be on support materials such as alumina, silica gel, aluminosilicates, activated carbon or zeolites.

The reaction is generally carried out in the presence of a catalytic proportion of the metal salt catalyst and will proceed with small amounts of the metal salt catalyst compounds hereinabove described. Generally the proportions of the metal salt catalyst used in the reaction will be equivalent to between about 0.001 to 5 weight per cent of the alkoxycycloalkene employed and are preferably employed in amounts between about 0.01 to 2 per cent by weight of the alkoxycycloalkene employed. Larger or smaller amounts may be employed at varied pressures and temperatures.

As mentioned hereinabove, a ligand or coordination complex compound of the metal catalyst may be employed in the process of the invention as a co-catalyst and thereby also achieve a pronounced increase in the selectivity for the oxalate ester. The ligands may be, for example, alkyl or aryl phosphines, arsines, iodides or stibines. The complexes of the metal catalysts which are suitable as co-catalysts in the process of the present invention include complex compounds of palladium, platinum, rhodium, cadmium, cobalt, zinc and copper. The complex compounds may contain one or more atoms of the said metals in the molecule and when more than one such atom is present, the metals may be the same of different. The mono- or poly-dentate ligands which are present in the molecule of the complex compounds and in which at least one of the electron-donating atoms is an atom of phosphorous, arsenic or antimony or an iodide ion containing a lone pair of electrons may be, for example, organophosphines, -iodides, -arsines and -stibines. Suitable mono-dentate ligands include alkyl phosphines such as trimethylphosphine and tributylphosphine, aryl-phosphines such as diethylphenyl-phosphine and radicals derived from such phosphines, for example the radical having the formula —P(CH$_3$)$_2$. Hydrocarbyloxy phosphines, i.e., phosphites, such as triphenyl phosphite may also be employed. Suitable polydentate ligands include tetramethyl diphosphinoethane and tetraphenyl diphosphinoethane. Exactly analogous derivatives of arsenic and antimony may be used; however, because of their greater ease of preparation and stability of the derived complexes, the hydrocarbyl derivatives of phosphorus are preferred. It is also preferred to employ alkali metal iodides, e.g., lithium iodide.

The complex compounds suitable for use in the process of the present invention may contain in the molecule, in addition to the ligands discussed above, one or more other atoms, groups or molecules, which are chemically bonded to the metal atom or atoms. Atoms which may be bonded to the metal include, for example, hydrogen, nitrogen and halogen atoms; groups which may be bonded to the metal include, for example hydrocarbyl, hydrocarbyloxy, carbonyl, nitrosyl, cyano and SnCl$_3$ —groups; molecules which may be bonded to the metal include, for example, organic isocyanides and isothiocyanates.

Examples of suitable complex compounds are those represented by the following formulae:

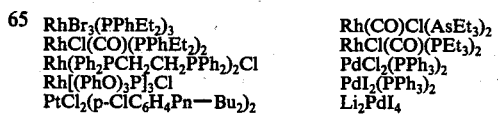

RhBr$_3$(PPhEt$_2$)$_3$
RhCl(CO)(PPhEt$_2$)$_2$
Rh(Ph$_2$PCH$_2$CH$_2$PPh$_2$)$_2$Cl
Rh[(PhO)$_3$P]$_3$Cl
PtCl$_2$(p-ClC$_6$H$_4$Pn—Bu$_2$)$_2$

Rh(CO)Cl(AsEt$_3$)$_2$
RhCl(CO)(PEt$_3$)$_2$
PdCl$_2$(PPh$_3$)$_2$
PdI$_2$(PPh$_3$)$_2$
Li$_2$PdI$_4$

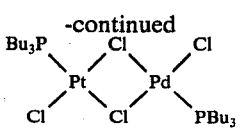

The complex compounds employed may be introduced into the reaction mixture as such, or they may be formed in situ from a suitable metal compound noted above and the desired ligand.

The ligand or complex compounds may be used in catalytic amounts of from 0 to 3 per cent preferably from 0.1 to 1 per cent by weight of the alkoxycycloalkene to be reacted although larger or smaller amounts may be employed at varied pressures or reaction rates.

The oxidizing salts which may be employed in an anhydrous condition and in catalytic amounts of from 0.1 to 10 weight per cent preferably 2 to 5 weight per cent in the process of the invention include the copper (II) salts such as the sulfates, trifluoroacetates, oxalates, or acetates preferably the copper (II) sulfates and trifluoroacetates. Representative oxidant salts include, for example, copper (II) sulfate, copper (II) trifluoroacetate, copper (II) acetate, copper (II) oxalate, copper (II) triflate and copper (II) fluorosulfonate. Excess chlorides in the form of oxidant salts are detrimental to the reaction system of the present invention. Iron (III) salts such as iron (III) sulfate may also be used in similar proportions in the instant process; the copper salts being preferred.

The amine salts which are employed in an anhydrous condition and in a catalytic amount of from 0.5 to 10 weight per cent preferably in a concentration ~5 weight per cent in the process of the invention include, for example, the ammonium and substituted ammonium sulfates, trifluoroacetates, and acetates, preferably the tertiary amine sulfates such as triethyl ammonium sulfate. Representative amine salts include, for example, diethylammonium sulfate, ethylammonium sulfate, butylammonium sulfate, ammonium sulfate, trimethylammonium sulfate, monomethylammonium sulfate, trimethyl ammonium hydrogen sulfate, ammonium acetate, ammonium trifluoroacetate, methyl-, ethyl- and butylammoniumtrifluoroacetate, etc.

The amine salts may be added as such or formed in situ in the required amounts upon the addition of an acid, such as sulfuric, benzene sulfonic, phosphoric, o-boric, p-toluene sulfonic, acetic or trifluoroacetic, to the reaction mixture while using greater than the required quantities of the amine base. The acids which may be used to form the salt include those which do not form a complex with the metal salt catalyst or, when employed, the metal salt oxidant compounds, inactivating the catalyst and oxidant. As indicated hereinabove the acids must be of sufficient strength, i.e., stronger than water, and such that the anion will not complex with the metal catalyst or oxidant salt. The salts which may be formed in situ may in themselves not necessarily be isolable and may exist in equilibrium in the reaction mixture under carbonylation reaction conditions. Thus, such salts could not be added per se but, as indicated above may be formed in situ upon the addition of a suitable acid to the reaction mixture containing amine.

Although not required, solvents, if desired, which are chemically inert to the components of the reaction system may be employed. Suitable solvents include, for example, organic esters such as ethyl acetate, n-propyl formate, isopropyl acetate, sec- and iso-butyl acetate, amyl acetate, cyclohexyl acetate, n-propyl benzoate, lower alkyl phthalates, etc. and the alkyl sulfones and sulfoxides such as propyl ethyl sulfoxide, diisopropyl sulfone, diisooctyl sulfoxide, acetone, cyclohexanone, methyl formate, etc.

As indicated above the reaction can be suitably performed by introducing the oxygen and carbon monoxide at a desired pressure into contact with the alcohol and alkoxycycloalkene reaction medium containing the specified reactants, catalyst, and amine and in addition an amine salt and oxidant salt and heating to the desired temperature. In general, a carbon monoxide pressure of about 500 psig to about 3000 psig partial pressure and preferably from 900 psig to about 2200 psig is employed. Stoichiometric quantities of carbon monoxide are generally employed. However, an excess of carbon monoxide may be employed, for example, in continuous processes where large excess of or high carbon monoxide requirements are generally utilized, and a suitable recycle of the carbon monoxide employed. The reaction will proceed at temperatures of from about 50° C. to 200° C. It is generally preferred to operate the process at temperatures in the range of 100° C. to 135° C. to obtain a convenient rate of reaction. Heating and/or cooling means may be employed interior and/or exterior of the reaction to maintain the temperature within the desired range.

At least stoichiometric amounts of oxygen or an oxygen containing gas such as air are generally employed and at any oxygen partial pressure such that the explosive range is avoided. Thus, the concentrations of oxygen should be low enough so that the reaction mixture is not potentially explosive. The Handbook of Chemistry and Physics, 48th Edition, 1967 indicates that the explosive limits of pure oxygen in carbon monoxide is 6.1 to 84.5 volume per cent and air in carbon monoxide to be 25.8 to 87.5 volume per cent.

The reaction time is generally dependent upon the alkoxycycloalkene and alcohol being reacted, temperature, pressure and on the amount and type of catalyst being charged as well as the type of equipment being employed. Reaction times will vary dependent on whether the process is continuous or batch.

The following examples are provided to illustrate the invention in accordance with the principles of this invention but are not to be construed as limiting the invention in any way except as indicated by the appended claims.

In the Examples which follow the reactions are run in a 500 ml stainless steel stirred autoclave. The liquid and solid materials are charged to the reactor (as solutions whenever possible). CO is charged to the reactor, to the desired pressure which is heated to reaction temperature. A CO flow rate is established and air flow added in such an amount that a potentially explosive gas mixture is never obtained in the reactor. When an exotherm is observed, cold water is circulated through the internal cooling coil to maintain the reaction temperature within ±1° C. Gas samples of the effluent are obtained periodically and analyzed for $CO_2$ by mass spectral analysis. The reactor is cooled to ambient temperature. During venting of the reactor, gas samples are obtained, and the composition determined by mass spectral analysis. The liquid product is analyzed by gas-liquid phase chromatography (glc) for the oxalate and carbonate ester.

EXAMPLE I

A solution of triethylamine (5.06 g; 50 mmoles), concentrated sulfuric acid (1.72g; 16.9 mmoles), methanol (40.4 g; 1.26 moles), and 1-methoxycyclohexene (70.6g; 0.63 mole) is charged to a 500 ml Magnedrive stirred autoclave fitted with a condenser ($-20°$ C.) and a liquid separator on the downstream side. Palladium (II) iodide (0.36 g; 1.0 mmole), lithium iodide (0.27 g; 2.0 mmoles), and copper (II) sulfate (5.17 g; 32.4 mmoles) is charged as solids. Carbon monoxide is charged to the autoclave to 1800 psig. The autoclave is heated to 100° C. with a stirring rate of 1500 rpm. The carbon monoxide flow rate (4.35 l./min.) is established, then the air flow (1.38 l./min.) started. An immediate exotherm is noted. A constant temperature is maintained with tap water ($\pm 1°$ C.). Gas samples of the effluent gases are collected periodically throughout the run and analyzed for $CO_2$ by mass spectral analysis.

The reaction is stopped after 135 minutes by cooling to ambient temperature with tap water. The gas flows are stopped, and the reactor is carefully vented. During venting, gas samples are collected and analyzed for $CO_2$.

After vacuum filtration of the reaction product, glc analysis shows the presence of dimethyl oxalate (0.64 mole), cyclohexanone, methanol, and trace amounts of dimethyl carbonate and 1-methoxycyclohexene. The filtered solid (4.9 g.) contains copper (II) oxalate hemihydrate.

EXAMPLE II

A mixture of 4.25 g. (42 mmoles) triethylamine, 1.72 g. (16.9 mmoles) concentrated sulfuric acid, 32.04 g. (1.0 mole) methanol, 100.0 g. (0.80 mole) 1-methoxy-4-methylcyclohexene, 0.18 g. (1.0 mmole) palladium (II) chloride, 0.27 g. (2.0 mmoles) lithium iodide and 5.17 g. (32.4 mmoles) of copper (II) sulfate is charged to the autoclave fitted with a condenser ($-20°$ C.) and liquid separator on the downstream side. CO is charged to the autoclave to 1600 psig. and the autoclave heated to 100° C. with stirring. A CO flow rate is established at 4.35 l./min. and an air flow rate of 1.38 l./min. started. A constant temperature is maintained ($\pm 1°$ C.) with tap water and the reaction run for 120 minutes and then stopped by cooling to ambient temperature with tap water. The gas flows are stopped and the autoclave vented at which time the gas samples are taken and analyzed for $CO_2$. The filtered reaction product analyzed by glc analysis shows a significant amount of dimethyl oxalate along with coproduct 4-methylcyclohexanone. Only a trace amount of dimethyl carbonate, as well as unreacted methanol and copper (II) oxalate hemihydrate are detected.

EXAMPLE III

The procedure of Example I is repeated. A mixture of 3.44 g. (34 mmoles) triethylamine, 3.38 g. (17 mmoles) triethylammonium hydrogen sulfate, 38.4 g. (1.20 moles) methyl alcohol, 70.6 g. (0.63 mole), 1-methoxycyclohexene, 0.38 g. (2.0 mmoles) copper (I) iodide, 0.54 g. (4.0 mmoles lithium iodide, and 5.17 g. (32.4 mmoles) of copper (II) sulfate is charged to the autoclave. The CO is charged to 2500 psig. The temperature is raised to 150° C. with stirring. A CO flow rate of 4.35 l./min. and an air flow rate of 1.38 l./min. are established. The temperature is maintained ($\pm 1°$ C.) and the reaction run for 140 minutes. Dimethyl oxalate (0.45 mole), cyclohexanone and a trace amount of dimethyl carbonate along with unreacted methyl alcohol are detected in the reaction product by glc analysis. Copper (II) oxalate hemihydrate is contained in the reaction product.

EXAMPLE IV

The procedure of Example I is repeated. A mixture of 2.25 g. (50 mmoles) ethylamine, 1.72 g. (16.9 mmoles) of concentrated sulfuric acid, 38.4 g. (1.20 moles) methyl alcohol, 70.6 g. (0.63 mole) 1-methoxycyclohexene, 0.24 g. (1.0 mmoles) palladium (II) sulfate 0.37 g. (2.0 mmoles) lithium iodide and 5.17 g. (32.4 mmoles) of copper (II) sulfate is charged to the autoclave. The CO is charged to 1800 psig. The temperature is raised to 135° C. with stirring. A CO flow rate of 4.35 l./min. and an air flow rate of 1.38 l./min. are established. The temperature is maintained ($\pm 1°$ C.) and the reaction run for 180 minutes. Dimethyloxalate, cyclohexanone, a trace amount of dimethyl carbonate, unreacted methanol are detected in the reaction product by glc analysis. Copper (II) oxalate hemihydrate is detected in the reaction product.

EXAMPLE V

The procedure of Example I is repeated. A mixture of 4.26 g. (50 mmoles piperidine, 1.72 g. (16.9 mmoles) of concentrated sulfuric acid, 41.6 g. (1.26 moles) methanol, 70.6 g. (0.63 mole) 1-methoxycyclohexene, 0.36 g. (1.0 mmole) palladium (II) iodide, 0.27 g. (2.0 mmoles) lithium iodide and 6.48 g. (16.2 mmoles) iron (II) sulfate is charged to the autoclave. The CO is charged to the autoclave to the pressure of 1500 psig. The temperature is raised to 100° C. with stirring and a CO flow rate of 4.35 l./min. and an air flow rate of 1.38 l./min. is established. The temperature is maintained and the reaction run for 180 minutes. Dimethyloxalate in significant quantities, cyclohexanone, dimethyl carbonate and unreacted methanol are detected in the reaction product. A trace amount of copper (II) oxalate hemihydrate is detected.

EXAMPLE VI

The procedure of Example I is repeated. A mixture of 7.02 g. (69.4 mmoles) triethylamine, 2.28 g. (23.2 mmoles) concentrated sulfuric acid, 38.4 g. (1.20 mole) methyl alcohol, 7.06 g. (0.63 mole) 1-methoxycyclohexene, 0.26 g. (2.0 mmoles) cobalt (II) chloride, 0.19 g. (1.42 mmoles) lithium iodide, 3.70 g. (23.2 mmoles) copper (II) sulfate is charged to the autoclave. CO is charged to the autoclave to a pressure to 2000 psig. The temperature is raised to 135° C. with stirring and a CO flow rate of 4.35 l./min. and an air flow rate of 1.38 l./min. are established. The temperature is maintained and the reaction run for a period of 180 minutes. Dimethyloxalate, cyclohexanone, a trace amount of dimethyl carbonate, along with unreacted methyl alcohol and 1-methoxy-cyclohexene and some copper (II) oxalate hemihydrate is detected in the reaction product.

EXAMPLE VII

A solution of tributylamine (9.27 g; 50 mmoles), concentrated sulfuric acid (1.72 g; 16.9 mmoles), methanol (40.4 g; 1.26 moles), and 1-methoxy-4-butylcyclohexene (106 g; 0.63 mole) is charged to a 500 ml. stainless steel stirred autoclave fitted with a condenser ($-20°$ C.) and a liquid separator on the downstream side. Palladium (II) iodide (0.36 g; 1.0 mmole), triphenylphosphine (1.05g; 4.0 mmoles), and copper (II) sulfate (5.17 g; 32.4 mmoles), are charged as solids. Carbon monoxide is charged to the autoclave at 1800 psig. The autoclave is heated to 110° C. with a stirring rate of 1500 rpm. The carbon monoxide flow rate (4.35 l./min.) is established, then the air flow (1.38 l./min.) started. An immediate exotherm is noted. A constant temperature is maintained with tap water (±1° C.). Gas samples of the effluent gases are collected periodically throughout the run and analyzed by mass spectral analysis for $CO_2$.

The reaction is stopped after 135 minutes by cooling to ambient temperature with tap water. The gas flows are stopped and the reactor carefully vented. During venting, gas samples are collected and analyzed for $CO_2$.

After vacuum filtration of the reaction product glc analysis shows the presence of dimethyloxalate (0.69 mole), 4-butylcyclohexanone, methanol and a trace amount of dimethylcarbonate and unreacted 1-methoxy-4-butylcyclohexene.

EXAMPLE VIII

The procedure of Example VII is repeated. A mixture of triethylamine (1.72 g; 17 mmoles), triethylammonium sulfate (5.11 g; 17 mmoles), ethyl alcohol (29.0 g; 0.63 mole), 1-methoxycyclohexene (70.6g; 0.63 mole), palladium (II) iodide (0.36 g; 1.0 mmole), lithium iodide (0.27 g; 2.0 mmoles), and copper (II) sulfate (5.17 g; 32.4 mmoles) is charged to the autoclave. The carbon monoxide is charged to 2000 psig. The autoclave is heated to 100° C. with a stirring rate of 1500 rpm. A carbon monoxide flow rate of 4.35 l./min. and an air flow rate of 1.38 l./min. are established. The temperature is maintained (±1° C.) and the reaction run for 140 minutes. Gas liquid chromatographic analysis shows the presence of dimethyloxalate, diethyloxalate, and methyl ethyl oxalate along with coproduct cyclohexanone and trace amounts of dimethylcarbonate and diethylcarbonate.

EXAMPLE IX

A mixture of 4.25 g (42 mmoles) triethylamine, 1.72 g. (16.9 mmoles) concentrated sulfuric acid, 24.0 g (0.75 mole) methanol, 105.2 g (0.75 mole) 1-methoxycyclooctene, 0.27 g (2.0 mmoles) zinc iodide, 0.27 g (2.0 mmoles) lithium iodide, and 5.17 g (32.4 mmoles) copper (II) sulfate is charged to the autoclave fitted with a condenser (−20° C.) and liquid separator on the downstream side. Carbon monoxide is charged to the autoclave to 1600 psig. and the autoclave heated to 100° C. with stirring. A carbon monoxide flow rate is established at 4.35 l./min. and an air flow rate of 1.38 l./min. started. A constant temperature is maintained (±1° C.) with tap water and the reaction run for 130 minutes and then stopped by cooling to ambient temperature with tap water. The gas flows are stopped and the autoclave vented and the effluent $CO_2$ analyzed. The filtered reaction product analyzed by glc analysis shows dimethyl oxalate (0.59 mole), unreacted methanol, cyclooctanone, along with a trace amount of dimethylcarbonate.

I claim:

1. A process for the preparation of oxalate esters which comprises reacting under substantially anhydrous conditions an alkoxycycloalkene having the formula

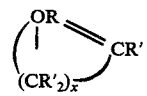

wherein R is an alkyl, or aralkyl group, R' is hydrogen or a straight or branched chain alkyl group which may be the same or different on the cyclic ring and x is an integer of from 3 to 6, with carbon monoxide, a monohydric saturated aliphatic, alicyclic or aralkyl alcohol, which may contain other substituents which do not interfere with the reaction, and oxygen, at a pressure of between about 500 psig and 3000 psig and at a temperature in the range of about 50° C. to 200° C in the presence of an effective amount of a catalyst selected from the group consisting of palladium, platinum, rhodium, cadmium, cobalt, zinc and copper salt compounds or mixtures thereof, and a catalytic amount of
  a. an aliphatic, cycloaliphatic, aromatic or heterocyclic amine or ammonia,
  b. a copper (II) or iron (III) oxidant salt compound, and
  c. an ammonium or substituted ammonium salt compound, and recovering the desired oxalate ester.

2. A process according to claim 1 wherein the catalyst salt compound is selected from the group consisting of palladium, platinum, rhodium, cadmium, cobalt and zinc, halides, oxalates, sulfates and acetates and copper halides.

3. A process according to claim 2 wherein the catalyst is selected from palladium sulfate, palladium chloride, palladium iodide, copper iodide, cobalt chloride and zinc iodide.

4. A process according to claim 3 wherein the catalyst is palladium iodide or palladium sulfate.

5. A process according to claim 3 wherein the catalyst is copper iodide.

6. A process according to claim 1 wherein the amine is employed in concentrations of from 0.1 to 5 weight per cent.

7. A process according to claim 6 wherein the amine is triethylamine.

8. A process according to claim 1 wherein the alkoxycycloalkene is selected from the group consisting of 1-methoxycyclohexene, 1-methoxy-4-methylcyclohexene, 1-methoxy-4-butylcyclohexene and 1-methoxycyclooctene.

9. A process according to claim 8 wherein the alkoxycycloalkene is 1-methoxycyclohexene.

10. A process according to claim 1 wherein the alcohol is selected from the group consisting of methyl alcohol and ethyl alcohol.

11. A process according to claim 10 wherein the alcohol is methyl alcohol.

12. A process according to claim 1 wherein the oxidant salt compound is copper (II) or iron (III) oxalate, sulfate, acetate or trifluoroacetate.

13. A process according to claim 12 wherein the oxidant salt is copper (II) sulfate.

14. A process according to claim 12 wherein the oxidant salt is iron (III) sulfate.

15. A process according to claim 1 wherein the ammonium salt compound is triethylammonium sulfate.

16. A process according to claim 1 wherein the ammonium salt compound is triethylammonium hydrogen sulfate.

17. A process according to claim 1 wherein the ammonium or substituted ammonium salt compound is formed in situ upon the addition of an acid to the reaction mixture containing an excess of amine over the required quantities of amine base for the reaction, said acid being of a strength stronger than water and such that the anion will not complex with the metal salt catalyst or metal oxidant salt compound.

18. A process according to claim 17 wherein said acid is sulfuric acid.

19. A process according to claim 1 wherein the reaction is carried out in the presence of a co-catalytic amount of an organic mono- or poly-dentate ligand or co-ordination complex of the metal catalyst selected from the group consisting of alkyl, aryl and halogen substituted phosphines, arsines, stibines, and iodides.

20. A process according to claim 19 wherein the ligand or co-ordination complex is triphenylphosphine.

21. A process according to claim 19 wherein the ligand or co-ordination complex is lithium iodide.

22. A process according to claim 1 wherein the pressure is between about 900 psig and 2200 psig and the temperature is in the range of about 100° C to 135° C.

23. A process according to claim 22 wherein the alkoxycycloalkene is 1-methoxycyclohexene, the catalyst is palladium iodide, the amine is triethylamine, the oxidant is copper (II) sulfate, the ammonium salt compound is triethylammonium sulfate, and the alcohol is methyl alcohol.

24. A process according to claim 23 wherein a catalytic amount of lithium iodide is added to the reaction mixture.

25. A process according to claim 1 wherein air is employed as a source of oxygen for the reaction.

26. A process according to claim 1 wherein the catalyst is supported.

* * * * *